(12) United States Patent
Tsai et al.

(10) Patent No.: US 7,807,043 B2
(45) Date of Patent: Oct. 5, 2010

(54) MICROFLUIDIC TEST DEVICE (75) Inventors: Fu Hsiung Tsai, San Diego, CA (US);
Jinn-nan Lin, San Diego, CA (US);
Chia-Lin Wang, San Diego, CA (US)

(73) Assignee: Oakville Hong Kong Company Limited, Central (HK)

( * ) Notice: Subject to any disclaimer, the term of this patent is extended or adjusted under 35 U.S.C. 154(b) by 1104 days.

(21) Appl. No.: 11/064,524

(22) Filed: Feb. 22, 2005

(65) Prior Publication Data
US 2005/0230252 A1 Oct. 20, 2005

Related U.S. Application Data (60) Provisional application No. 60/547,274, filed on Feb. 23, 2004.

(51) Int. Cl.
*G01N 27/327* (2006.01)
(52) U.S. Cl. .............. 205/778; 204/403.01; 204/403.02
(58) Field of Classification Search ............ 204/403.01, 204/403.02, 403.06, 403.11; 205/778
See application file for complete search history.

(56) References Cited

U.S. PATENT DOCUMENTS

| 3,838,033 | A | | 9/1974 | Mindt |
| 4,484,987 | A | * | 11/1984 | Gough ........................ 205/778 |
| 4,545,382 | A | | 10/1985 | Higgins |
| 4,711,245 | A | | 12/1987 | Higgins |
| 4,810,658 | A | | 3/1989 | Shanks |
| 4,929,545 | A | | 5/1990 | Freitag |
| 4,978,503 | A | | 12/1990 | Shanks |
| 4,999,582 | A | | 3/1991 | Parks |
| 5,120,420 | A | | 6/1992 | Nankai |
| 5,141,868 | A | | 8/1992 | Shanks |
| 5,271,895 | A | | 12/1993 | McCroskey |
| 5,288,636 | A | | 2/1994 | Pollmann |
| 5,320,732 | A | | 6/1994 | Nankai |
| 5,382,346 | A | | 1/1995 | Uenoyama |
| 5,429,735 | A | | 7/1995 | Johnson |

(Continued)

FOREIGN PATENT DOCUMENTS

EP        0170375        8/1985

(Continued)

*Primary Examiner*—Kaj K Olsen
(74) *Attorney, Agent, or Firm*—Fred C. Hernandez; Mintz, Levin, Cohn, Ferris, Glovsky and Popeo P.C.

(57) ABSTRACT

The present invention provides biosensor test devices for measuring the presence or amount of an analyte in a biological fluid. The devices have a base plate that has an electrode system embedded therein, and a hydrophilic porous material situated on the base plate. A hydrophobic protective layer is situated on the hydrophilic porous material, and a cover is placed on the hydrophobic protective layer to complete the device. Some embodiments also use an insulating layer, which can be situated between the base layer and the hydrophilic porous material. The cover of the device has an opening present therein, situated over the electrodes, so that the electrodes communicate with the exterior of the device through the groove. The insulating layer can also have a groove situated therein, which in one embodiment is placed to align with the groove in the cover. The invention also provides methods of manufacturing the devices, and methods of using them.

25 Claims, 4 Drawing Sheets

U.S. PATENT DOCUMENTS

| | | | |
|---|---|---|---|
| 5,437,999 | A | 8/1995 | Diebold |
| 5,496,453 | A | 3/1996 | Uenoyama |
| 5,508,171 | A | 4/1996 | Walling |
| 5,509,410 | A | 4/1996 | Hill |
| 5,575,403 | A | 11/1996 | Charlton |
| 5,582,697 | A | 12/1996 | Ikeda |
| 5,620,579 | A | 4/1997 | Genshaw |
| 5,627,075 | A | 5/1997 | Bateson |
| 5,628,890 | A | 5/1997 | Carter |
| 5,650,062 | A | 7/1997 | Ikeda |
| 5,660,791 | A | 8/1997 | Brenneman |
| 5,682,884 | A | 11/1997 | Hill |
| 5,696,314 | A * | 12/1997 | McCaffrey et al. .......... 205/778 |
| 5,708,247 | A | 1/1998 | McAleer |
| 5,727,548 | A | 3/1998 | Hill |
| 5,762,770 | A | 6/1998 | Pritchard |
| 5,798,031 | A | 8/1998 | Charlton |
| 5,820,551 | A | 10/1998 | Hill |
| 5,951,836 | A | 9/1999 | McAleer |
| 5,997,817 | A | 12/1999 | Crismore |
| 6,120,676 | A | 9/2000 | Heller |
| 6,129,823 | A | 10/2000 | Hughes |
| 6,214,205 | B1 | 4/2001 | Willner |
| 6,225,078 | B1 | 5/2001 | Ikeda |
| 6,241,862 | B1 | 6/2001 | McAleer |
| 6,248,229 | B1 | 6/2001 | Meade |
| 6,258,229 | B1 | 7/2001 | Winarta |
| 6,287,451 | B1 | 9/2001 | Winarta |
| 6,329,161 | B1 | 12/2001 | Heller |
| 6,451,372 | B2 | 9/2002 | Hasegawa |
| 6,458,258 | B2 | 10/2002 | Taniike |
| 6,461,496 | B1 | 10/2002 | Feldman |
| 6,484,046 | B1 | 11/2002 | Say |
| 6,491,803 | B1 | 12/2002 | Shen |
| 6,540,890 | B1 | 4/2003 | Bhullar |
| 6,541,216 | B1 | 4/2003 | Wilsey |
| 6,551,494 | B1 | 4/2003 | Heller et al. |
| 6,591,125 | B1 | 7/2003 | Buse |
| 6,599,406 | B1 * | 7/2003 | Kawanaka et al. ..... 204/403.02 |
| 6,599,407 | B2 | 7/2003 | Taniike |
| 6,679,841 | B2 | 1/2004 | Bojan |
| 6,695,958 | B1 * | 2/2004 | Adam et al. ........... 204/403.01 |
| 6,773,563 | B2 * | 8/2004 | Matsumoto ................ 204/401 |
| 6,908,593 | B1 | 6/2005 | Shartle |
| 6,913,668 | B2 | 7/2005 | Matzinger |
| 6,939,312 | B2 | 9/2005 | Hodges |
| 6,942,769 | B2 * | 9/2005 | Cheng et al. ................ 204/400 |
| 2001/0006149 | A1 | 7/2001 | Taniike |
| 2001/0006150 | A1 | 7/2001 | Taniike |
| 2003/0196894 | A1 | 10/2003 | Cai |
| 2003/0205464 | A1 | 11/2003 | Taniike |
| 2004/0026266 | A1 | 2/2004 | Atkinson |
| 2004/0043477 | A1 | 3/2004 | Schibli |
| 2004/0045821 | A1 | 3/2004 | Cui |
| 2004/0067166 | A1 | 4/2004 | Karinka |
| 2004/0081752 | A1 | 4/2004 | Lin |

FOREIGN PATENT DOCUMENTS

| | | |
|---|---|---|
| EP | 0170376 | 3/1989 |
| EP | 0390390 | 10/1990 |
| EP | 0171148 | 4/1991 |
| EP | 0359831 | 8/1995 |
| EP | 0422708 | 9/1996 |
| EP | 0874984 | 11/2001 |
| EP | 1113264 | 5/2002 |
| EP | 1343007 | 9/2003 |
| EP | 0880692 | 1/2004 |
| EP | 1402812 | 3/2004 |
| EP | 1445605 | 8/2004 |
| WO | WO 86/00135 | 1/1986 |
| WO | WO 86/00138 | 1/1986 |
| WO | WO 86/00141 | 1/1986 |
| WO | WO 99/13100 | 3/1999 |
| WO | WO 03/056345 | 7/2003 |
| WO | WO 2004/062494 | 7/2004 |

* cited by examiner

MICROFLUIDIC TEST DEVICE

This application claims priority to U.S. provisional patent application Ser. No. 60/547,274, filed Feb. 23, 2004, which is hereby incorporated by reference in its entirety, including all tables, figures, and claims.

FIELD OF THE INVENTION

The present invention relates to biosensors having improved sample application and measuring properties and methods of their manufacture and use.

BACKGROUND OF THE INVENTION

The following Background of the Invention is intended to aid the reader in understanding the invention and is not admitted to be prior art.

In recent years, medical care has changed dramatically, from primarily using clinical laboratory analysis of samples to rapid point of care testing in the doctor's office or at the patient's bedside. Disposable enzyme biosensors are frequently used to perform these rapid tests. Taking glucose testing as an example, in-home testing by the patient is now commonplace and a necessity for proper disease management. To conduct an in-home test using a glucose biosensor, the diabetic patient lances the finger to withdraw a small amount of blood. The patient applies the blood to the biosensor test strip and within a few seconds the meter accompanying the biosensor records electrical data from the biosensor and calculates the glucose concentration in the patient's blood. This information is used to make decisions about when and how much insulin to administer.

In spite of the advances achieved in rapid and accurate measurement of metabolites, patient compliance remains a significant problem due to the pain associated with blood withdrawal. To reduce pain and increase patient compliance, new lancet devices that obtain blood from the forearm or thigh are now in use. These lancet devices cause less pain because there are fewer nerve endings in these locations of the body. However, there are also fewer surface blood vessels, which make it difficult to obtain enough blood for the test. In general, patients find that if the lancet device is set for less pain, less blood is obtained. This is a problem because prior art biosensors require several microliters of blood to correctly fill the capillary channel and function. If the volume of sample is too low, the capillary channel will not fill properly. The test will either not work or will give inaccurate results. Then, the patient will have to throw the improperly filled test strip away, and start over. The patient will have to stick himself with the lancet at least one more time and use a second test strip. This situation is very difficult and upsetting for some patients and reduces their compliance in blood monitoring. Consequently, these patients have difficulty monitoring and correctly treating their disease.

Several examples of biosensors are available. For example, U.S. Pat. Nos. 5,120,420 and 5,320,732 to Nankai, U.S. Pat. No. 5,141,868 to Shanks and U.S. patent application 2003/0196894 to Cai disclose disposable glucose biosensors. These biosensors are constructed of two plastic layers laminated to spacers and thereby held together. This structure forms a vented capillary channel that draws an applied sample into the interior and onto a test area. Venting is required for the capillary channel to function properly. When the sample flows into the channel by capillary flow, the sample comes into contact with an enzyme layer and electrodes, which detect and optionally measure an analyte in the sample.

Accordingly, there is a persistent need in the art for biosensors and methods that provide for improved sample application and measuring properties.

SUMMARY OF THE INVENTION

The present invention provides test devices for measuring the presence or amount of an analyte in a biological fluid. The test devices contain material components, which are assembled to form the device. These devices require a minimum of sample volume, and can be used to accurately determine the quantity of an analyte in a fluid sample. The devices have a base plate that has an electrode system embedded therein, and a hydrophilic porous material situated on the base plate. A hydrophobic protective layer is situated on the hydrophilic porous material, and a cover is placed on the hydrophobic protective layer. In one embodiment the protective layer is porous and allows for the passage of air from the reaction chamber to the exterior of the device. Some embodiments also use an insulating layer, which can be situated between the base layer and the hydrophilic porous material. The cover of the device has an opening present therein, which is situated over the electrodes so that the electrodes communicate with the exterior of the device through the opening. The insulating layer can also have an opening situated therein, which in one embodiment is a groove placed to align with the opening in the cover. Thus, in these embodiments the electrodes communicate with the exterior of the device through the groove and the opening in the cover. The layer of hydrophilic porous material and the hydrophobic protective layer do not necessarily cover the entire base plate, but cover at least that area above the groove in the insulating layer (when present) or the area below the opening in the cover. The invention also provides methods of manufacturing the devices, and methods of using them.

In a first aspect, the present invention provides microfluidic devices for determining the amount of an analyte in a sample. The devices have a base plate having an electrode system having at least two electrodes in a dielectric material. A reaction layer is present on at least one of the electrodes having reagents for producing a detectable signal in response to a quantity of analyte in the sample. The devices also have a hydrophilic porous material which holds a liquid sample in contact with the base plate, and a hydrophobic protective layer disposed on the hydrophilic porous material. The device also contains a cover made of a dielectric material which has a proximal end and a distal end. The cover is situated on the hydrophobic protective layer and has an opening which provides for communication between the electrodes and the exterior of the device. In one embodiment the opening is a groove extending from the proximal end towards the distal end of the device.

In one embodiment the device also has an insulating layer disposed between the base plate and the hydrophilic porous material, and which has a groove. In one embodiment the groove is situated in alignment with the opening in the cover of the device. The opening in the cover may also be present as a groove, and the two grooves may be aligned. The at least two electrodes of the device can be three electrodes, for example, a working electrode, a reference electrode, and a counter electrode. In various embodiments the base plate can be made of a variety of materials, for example, carbon, polystyrene, polycarbonate, and a polyester. The hydrophilic porous material can also be made of a variety of materials, for example, a gel, a glass fiber, a porous plastic, a cellulosic material, or a polyester. The hydrophilic porous material can be present in the form of a mesh. In one embodiment the polyester is polyethylene terephthalate (PET). In one embodiment the hydrophilic porous material has a hydrophilic surface.

The hydrophobic protective layer of the device can also be made of a variety of materials in different embodiments, for example, a gel, glass fiber, a porous plastic, a cellulosic material, or a polyester. In one embodiment the hydrophobic protective layer is present in the form of a mesh.

In various embodiments the cover and/or the insulating layer is made of a hydrophobic, non-conductive material, for example, an ink, adhesive, adhesive tape, a plastic, a celluloid material, glass, or a non-conductive foil.

In one embodiment the hydrophilic porous material and the hydrophobic protective layer cover the proximal portion of the base plate, and the at least two electrodes communicate with the exterior of the device through the opening in the proximal end of the cover. In another embodiment the hydrophilic porous material and/or the hydrophobic protective extend across the groove and the opening in the cover of the device (which in one embodiment is a second groove. The hydrophobic protective layer can be situated between the hydrophilic porous material and the cover, and extend across the opening in the cover. The reaction layer of the device can contain an enzyme or other reagents for detecting the quantity of an analyte in the fluid sample. In one embodiment the reaction layer contains glucose oxidase.

The electrodes can be arranged in any suitable order. In one embodiment the counter electrode is closest to the proximal end of the base plate, and the reference electrode is farthest from the proximal end of the base plate. The working electrode can be situated in between the counter and reference electrodes. In one embodiment of the device, the hydrophilic porous material is disposed on the base plate, the hydrophobic protective layer is disposed on the hydrophilic porous material, and the cover is disposed on the hydrophobic protective layer.

In another aspect the present invention provides methods of manufacturing a microfluidic device. The methods involve placing a reagent formulation for conducting an assay onto at least one electrode of a base plate comprising an electrode system having at least two electrodes in a dielectric material, applying a hydrophilic porous material to the base plate, affixing a hydrophobic protective layer to the hydrophilic porous material, affixing a cover made of a dielectric material and having a proximal end and a distal end onto the hydrophobic protective layer. The cover contains an opening (e.g., a groove) allowing communication between the electrodes and the exterior of the device. In one embodiment the opening is a groove extending from the proximal end towards the distal end, and the electrodes communicate with the exterior of the device through the groove in the cover and the groove in the insulating layer.

In one embodiment the methods further involve placing an insulating layer on the base plate before applying the hydrophilic porous material, and the insulating layer has a groove (which may be situated in alignment with the first groove of the cover) and is made of a hydrophobic, dielectric material. The insulating layer can be placed by a variety of methods, for example, screen printing, ink jet printing, application of adhesive or adhesive tape, lamination of the layers of material, heat sealing, and ultrasonic welding can all be used to place the layer. However, other methods known in the art will also be useful for placing the layer. These methods are also useful for placing any of the components or layers of the device. The hydrophilic porous material and the hydrophobic protective layer can be placed to cover at least the proximal portion of the base plate, and the base plate contains at least two electrodes that communicate with the exterior of the device through the opening in the proximal end of the cover. In various embodiments the hydrophilic porous material, the hydrophobic protective layer, and the cover can be placed on the base plate by any suitable method, such as those described above.

In another aspect the present invention provides methods of determining the concentration of an analyte in a fluid sample. The methods involve placing a portion of the sample on a test device of the present invention, inserting the test device into an electronic detection system so that the test device is connected to the detection system through the contact leads of the test device, and determining the concentration of the analyte in the fluid sample.

The summary of the invention described above is not limiting and other features and advantages of the invention will be apparent from the following detailed description, as well as from the claims.

DETAILED DESCRIPTION

The device of the present invention includes a base plate, a hydrophilic porous material, a hydrophobic protective, and a cover. In some embodiments the device can also contain an insulating layer. The components of the device can be laminated together, or in other embodiments can be printed onto the base plate to form the device, or can be affixed to each other using adhesives. The base plate 101, insulating layer 111 (when present), and hydrophilic porous material 115 form a sample intake port 201, where fluid sample is introduced into the device in preparation for analysis. The sample intake port can be present in the proximal end of the device, so that sample introduced into the sample intake port is held onto the electrodes of the device in the reaction chamber.

In use the proximal end 109 of the device, which contains the sample intake port, is touched to a droplet of test sample. In one embodiment the test sample is whole blood, which the user can obtain by pricking a finger. When the sample intake port is touched to a droplet of sample fluid, the sample fluid is drawn into the reaction chamber of the device and is held on the electrodes of the device. The device is then prepared for insertion into an electronic reader, which will direct an electrical current through the electrodes, and thereby measure the passage of current and determine the presence or amount of analyte in the sample.

Base Plate

Figure 1:
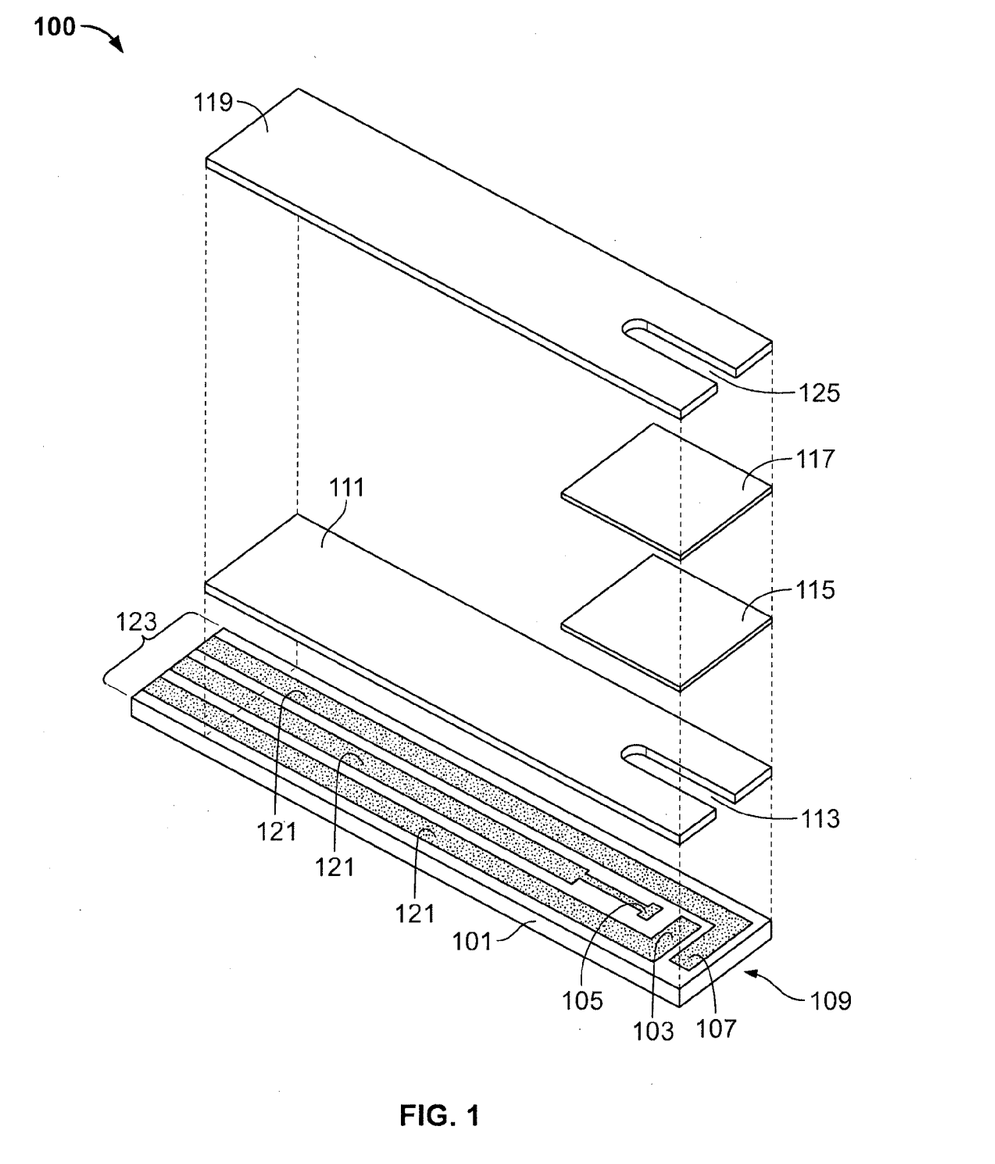
FIG. 1 illustrates the arrangement of the layers of a device of the invention and the reaction chamber defined by the layers, which is bounded by the base plate 101, sides of the groove 113, and hydrophilic porous material 115.
Figure 2:
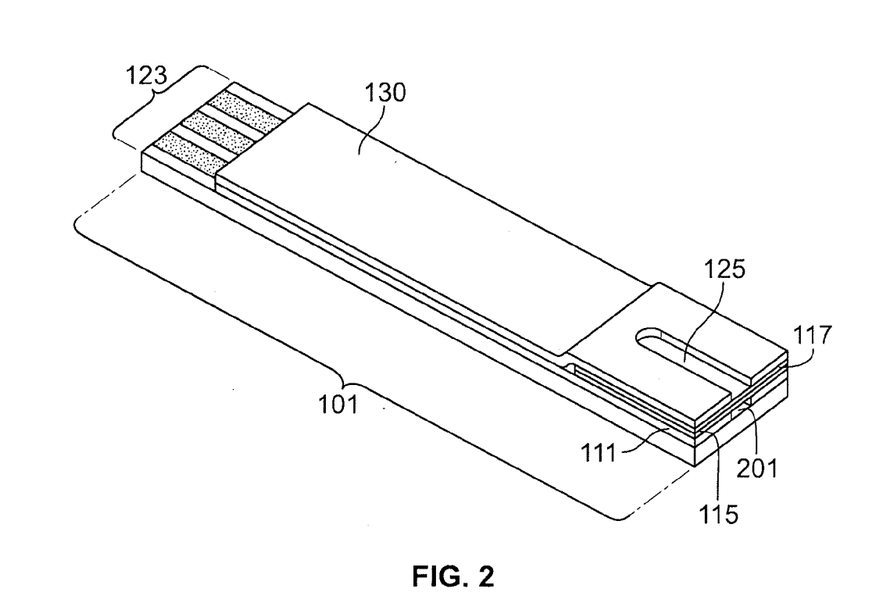
FIG. 2 illustrates the arrangement of components of a device of the invention.
Figure 3:
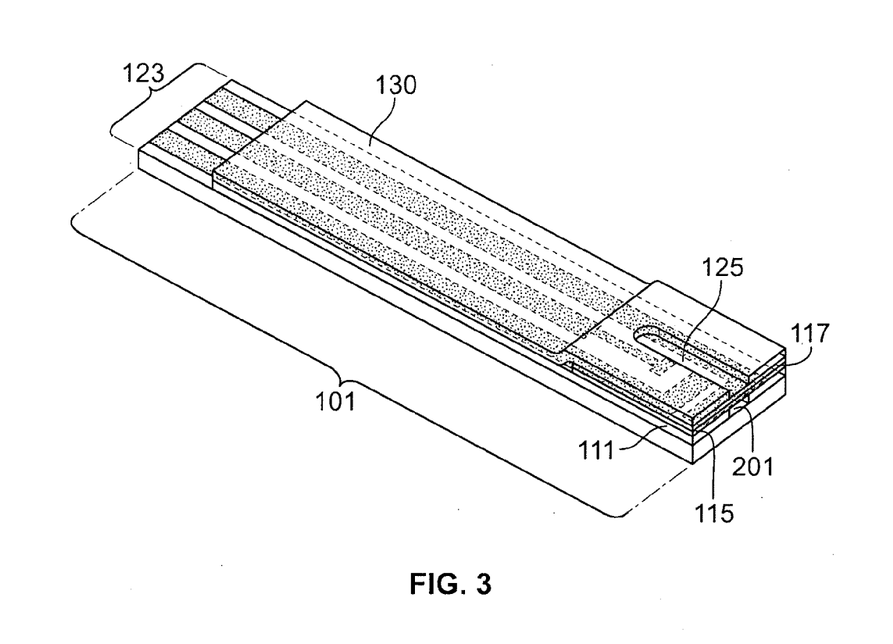
FIG. 3 provides another illustration of a device of FIG. 2, with the upper layers drawn in outline, and illustrating the position of the contact leads 123 in one embodiment.
Figure 4:
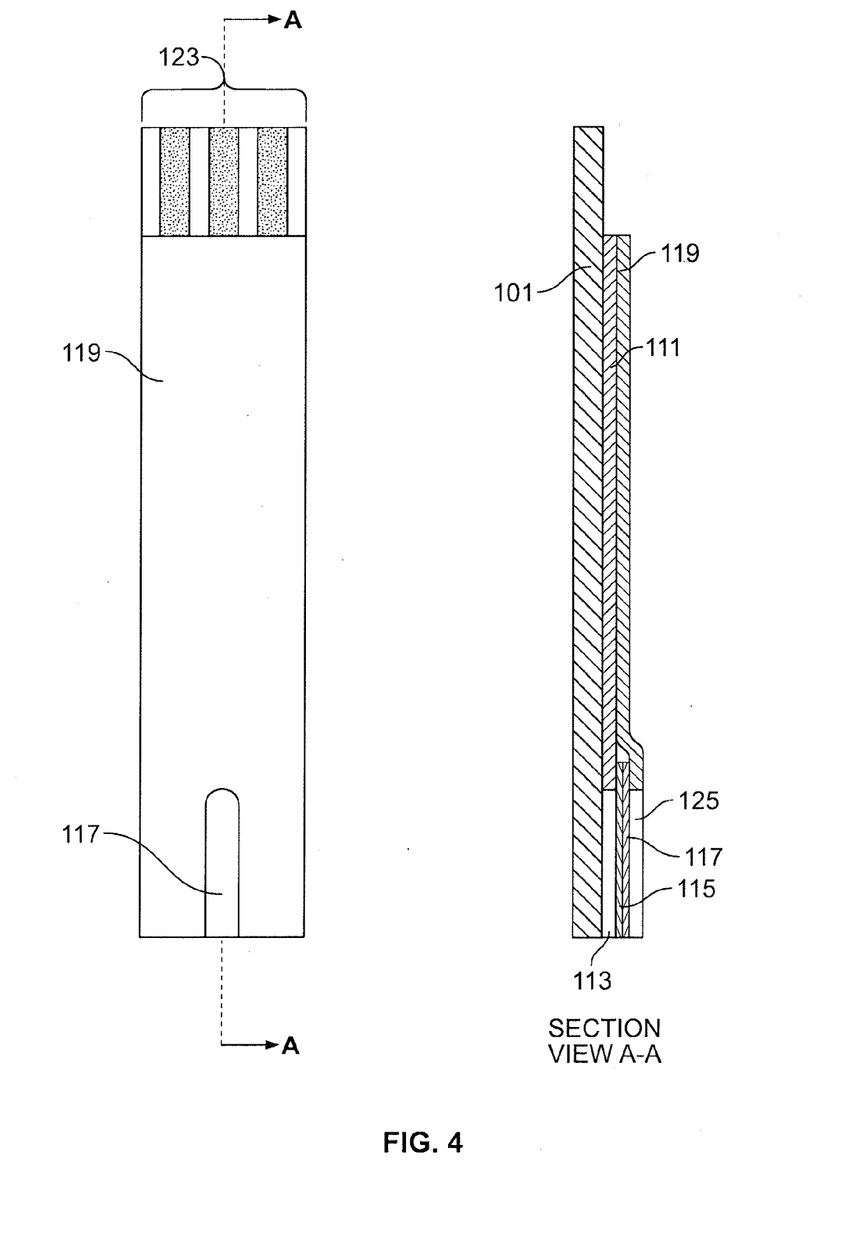
FIG. 4 is a top view and a cross-section view of a device of FIG. 1.

With reference to FIG. 1, the base plate 101 of the device is depicted containing the electrodes (103, 105, 107), which are used to electronically determine the presence or amount of an analyte of interest present in a fluid sample. At least two electrodes are present in the device, but the base plate can contain three (or more) electrodes (as depicted). The base plate 101 can be constructed of a variety of materials, such as carbon, polystyrene, polycarbonate, polyvinyl chloride resin, and a polyester. In one embodiment the base layer is constructed of polyethylene terephthalate (PET). A strip of PET 5 mil thick provides an appropriate support, as does a 14 mil white film PET. Of course many different thicknesses will also function well in the invention. The base plate provides a support for receiving the electrodes and electrode leads.

In one embodiment the electrodes and electrode leads are printed on the base layer. Ag/AgCl, carbon inks (graphite), palladium, gold, platinum, iridium, doped indium tin oxide, stainless steel, and other suitable conducting materials can be used. The electrodes can also be made of combinations of these materials. For example, one portion of the electrode can be one material and another portion of the same electrode can be another material. The electrodes can be arranged on the base layer in any desirable format. In one embodiment the device has three electrodes—a working electrode, a counter electrode, and a reference electrode. In one embodiment the counter electrode 107 is placed closest to the proximal end 109 of the device, and the reference electrode 105 is placed the furthest from the proximal end of the device. The working electrode 103 can then be placed between the counter electrode 107 and reference electrode 105. In other embodiments, two electrodes (or more) can be present, or the electrodes can be arranged in other formats. The base plate also contains leads 121 for the electrodes, and has contact leads 123 at one end. In one embodiment the contact leads are present at the distal end of the device. The contact leads can be used to connect the device to a reader, which directs current through the electrodes to measure the presence or quantity of an analyte of interest in a liquid sample. In the present context the term "proximal" end refers to the end of the device where the electrodes are located, while the "distal" end refers to the end of the device where the contact leads are located. While FIG. 1 depicts one system of electrodes, other designs are possible and are also within the scope of the invention. For example, the electrodes can be designed so that the sample intake port will be positioned on either side of the sensor. In those embodiments the sample intake port would thus still be present towards the proximal end of the sensor, but not necessarily at the edge on the end.

In one embodiment the hydrophilic porous material and hydrophobic protective layer cover the entire sensor, but in other embodiments they cover only the proximal end of the device. The "proximal end" of the device is that end farthest from the contact leads and the end on which the electrodes are located. In various embodiments the proximal end of the device is the one-third portion of the device closest to the electrodes and farthest from the contact leads, as measured lengthwise. In various other embodiments the proximal end is the one-fourth, or one-fifth or one-half of the portion of the device closest to the electrodes and farthest from the contact leads. In one embodiment the hydrophilic porous material and hydrophobic protective layer cover at least the space within the groove of the insulating layer (when present) and the space beneath the opening in the cover.

Reaction Layer

A reaction layer can be placed on at least one of the electrodes, but can cover two or all of the electrodes. The reaction layer contains one or more reagents for measuring the presence or amount of an analyte of interest in the fluid sample. The reagents present in the reaction layer will depend on the specific assay being conducted. Any analyte for which there exists reagents that will produce an electrically detectable signal when the analyte is present can be included in the reagent layer. In one embodiment the reaction layer contains an oxidoreductase and an electron acceptor, for analyzing the sample and generating a substance through the reaction that is detectable by the electrode system. The reaction layer is desirably contained on the base plate, but it can also be present anywhere within the reaction chamber, which is the volume defined by the base plate 101, the inner surface of the groove of the insulating layer 113 (when the insulating layer is present), and the mesh of the hydrophilic, porous material 115. The term "groove" refers to a channel, depression or notch. The groove can be of any shape, but in one embodiment will be a rounded channel or depression, as depicted in the Figures. The groove can extend from any side of the insulating layer or cover over at least one of the electrodes of the device.

In one embodiment the analyte of interest is glucose present in blood (e.g., whole blood). In this embodiment, the reaction layer can include glucose oxidase. The reagents can also include a binder. In one embodiment the binder is hydroxyethylcellulose (HEC). The NATROSOL® HEC M polymer can also be used to bind the components of the reagent layer. This binder is hydrophilic and can also be used to mix with the incoming blood sample so that an electrochemical cell is established in a period of seconds. Other materials can also be used as the binder, for example, hydroxymethylcellulose and hydroxypropylcellulose. A stablilizer can also be included in the reagent formulation. In one embodiment polyethylene glycol (PEG) can be included. PEG can also facilitate a rapid response in the assay. In various other embodiments the reaction layer can also contain mediators, surfactants, stabilizers, and polymers, and any other reagents that are useful for conducting the assay.

Insulating Layer

In some embodiments an insulating layer 111 is present on the base layer 101. But in other embodiments the device will function without an insulating layer. When present, the insulating layer can contain a groove 113 present at the proximal end 109 of the device, and which establishes a boundary of the reaction chamber. In those embodiments where no insulating layer is present, the reaction chamber is that space within the mesh of the hydrophilic porous material. The groove in the insulating layer can also be situated to open to either side of the device, and need not be situated extending from the proximal towards the distal end of the device in all embodiments.

In some embodiments the insulating layer can be a plastic or other dielectric material. Examples of suitable dielectric materials for use as the insulating layer include dielectric inks, adhesives, an adhesive tape or film, plastics, celluloid materials, glass, and dielectric foils. In some embodiments the insulating layer will also contain an adhesive to secure it to the base layer. The insulating layer can also be a two-sided adhesive tape, with one side secured to the base layer and the other secured to the hydrophilic porous material and/or cover of the device.

In one embodiment the insulating layer is ARcare® 7840 (Adhesives Research, Inc., Glen Rock, Pa.), which is a double-sided AS-110 acrylic resin coated adhesive tape. The tape is coated on a 2 mil white PET plastic support to form the base plate and insulating layer. The adhesive coating on each side is 0.70 mil. In this embodiment, the thickness of the groove or channel formed is 3.4 mil. When present, the groove of the insulating layer assists in drawing the fluid sample into contact with the electrodes.

Hydrophilic Porous Material

The hydrophilic porous material 115 can be made of any of a variety of materials, for example, a gel, glass fibers, porous plastic, a porous membrane, a polyester, a polyamide, and a cellulose material (e.g., cellulose or cellulose acetate). The hydrophilic porous material serves to hold the liquid sample in contact with the reaction chamber, and may also serve to wick the liquid sample into the reaction chamber. The hydrophilic porous material can be in the form of a mesh, and has a hydrophilic surface. Thus, the hydrophilic porous material can be made of a material that is hydrophobic, but has a surface modified to have hydrophilic properties. The material can also be made of a material that naturally has hydrophilic properties. In one embodiment, the hydrophilic porous material has an adhesive applied to it in order to affix it to the surface of the base plate or insulating layer. It can also have a layer of adhesive for attachment of the porous hydrophobic protective.

In one embodiment the hydrophilic porous material can be a mesh made of a polyester, for example a woven polyester mesh of polyethylene terephthalate (PET). The surface of the material can be modified by chemically attaching a hydrophilic molecule to it. For example, in embodiments where PET polyester is the hydrophilic porous material, a surfactant can be chemically attached to the PET to form a hydrophilic surface on the PET. The surfactant can be any surfactant that can be bound to the surface of the hydrophilic porous material and has a hydrophilic end. Examples of suitable surfactants include sodium dodecyl sulfate, TRITON X-100®, polyethylene glycols, and dioxanes (e.g., 1,4-dioxane). The hydrophilic porous material is a material that draws a fluid and transports it along the material. A mesh is a form of material. In one embodiment the mesh is a bundle of fibers, which can be loosely twisted, braided, or woven to form the hydrophilic porous material. However, a mesh can be any porous material that allows the passage of air through it. A mesh also supports the transport and flow of fluid through the material.

Protective Layer

In one embodiment the protective layer 117 is situated between the hydrophilic porous material 115 and the cover 119. Thus, it can be situated directly on top of the hydrophilic porous material. The protective layer protects the reaction area from contamination with substances that may be introduced by the user handling the device. In one embodiment the protective layer is porous to allow for the passage of air. The protective layer can also be hydrophobic, and serves to retain sample in the reaction area and impede movement of sample upward and out of the reaction area. The protective layer can be made of any suitable material. Various examples of appropriate materials include a gel, glass fiber, porous plastics, and a cellulosic material. In one embodiment the protective layer is hydrophobic, and may be present in the form of a mesh. In some embodiments the protective layer also contains an adhesive to bind it to the base layer and hydrophilic porous material. In one embodiment the protective layer is not coated with surfactant or any other substance that confers hydrophilic properties to the surface. The term "hydrophobic" refers to a material having surface groups that do not form significant hydrogen bonding with water. Hydrophobic materials are not soluble in water (although they may still have some slight solubility). In general, water will form a bead when placed on a hydrophobic material, due to repulsive molecular forces between the material and water molecules. Materials that are "hydrophilic" have surface groups that do form significant hydrogen bonds with water. When water is placed on these materials, it is absorbed by or held within the material, or is moved through the material. Hydrogen bonds are significant when they constitute an important portion of the attractive forces between molecules.

Cover

In one embodiment the cover 119 of the device is made of a dielectric material. The materials selected can be any of the same as those selected for the insulating layer. In one embodiment the cover of the device also has an opening present towards the proximal end of the device to allow the communication of air between the reaction chamber and the exterior of the device. The opening can be a groove 125 (as depicted in the embodiment of FIG. 1), but in other embodiments the opening can be any type of opening that allows the passage of air from the reaction chamber out of the device. In some embodiments, the cover can be a dielectric ink, which can be printed onto the device. The cover can also contain an adhesive to affix it to the hydrophobic protective layer and insulating layer (when present), and base plate. The opening in the cover can be situated extending from the proximal to the distal end of the cover, as depicted in FIG. 1. But the opening can also be situated to open from either side of the cover, and can also be a hole in the cover allowing for the exit of air from the reaction chamber and communication between the reaction chamber and exterior of the device. The opening can also be aligned with the groove in the insulating layer to provide for communication between the electrodes and the exterior of the device.

Reaction Area

The reaction chamber 201 contains the reagent layer, which is generally situated on at least one of the electrodes. The reaction chamber is bounded by the base plate, the sides of the groove of the insulating layer (when present), and the hydrophilic porous material. When fluid sample is introduced into the reaction chamber through the sample intake port, the reagents are solubilized in the sample, and the electrochemical reaction is prepared to begin.

Analytes and Sample Fluids

Using the present invention, any analyte can be detected in a fluid sample for which there can be designed an electrochemical assay. Some examples of analytes that can be detected using the present invention are glucose, lactate, urea, bicarbonate, 3-hydroxybutyric acid (3-HBA), amino acids (e.g., L-glutamate, aspartate, L-lysine), ammonium, sodium, calcium, trace metals, and any other analyte for which there can be designed an electrochemical assay. The reagents in the reaction layer will of course be changed to those appropriate for testing for the analyte of interest. When 3-HBA is the analyte, mediators such as $K_3Fe(CN)_6$, ferrocene, hexacyanpferrate, and enzymes such as 3-HBA dehydrogenase and diaphorase, and the cofactor NAD can be included in the reagent layer.

Any sample fluid sample (or fluidized sample) can be analyzed using the devices. Examples of sample fluids that can be tested include whole blood, blood serum, blood plasma, urine, and saliva. Clinical samples, biological samples, and environmental samples can also be tested, whether they are supplied as fluids or must be liquefied before analysis. The sample fluid can also be a buffer, or a solution or suspension containing a solid or gaseous biological material.

The present biosensors and methods can be used to qualitatively or quantitatively detect any analyte or enzyme. For example, the analyte to be assayed can be macromolecules such as peptides, proteins, e.g., antibodies or receptors, oligonucleotides, nucleic acids, vitamins, oligosaccharides, carbohydrates, lipids, or small molecules, or a complex thereof.

Exemplary proteins or peptides include enzymes, transport proteins such as ion channels and pumps, nutrient or storage proteins, contractile or motile proteins such as actins and myosins, structural proteins, defense proteins or regulatory proteins such as antibodies, hormones and growth factors. Exemplary nucleic acids include DNA, such as A-, B- or Z-form DNA, and RNA such as mRNA, tRNA and rRNA. The nucleic acids can be single-, double- and triple-stranded nucleic acids. Exemplary vitamins include water-soluble vitamins such as thiamine, riboflavin, nicotinic acid, pantothenic acid, pyridoxine, biotin, folate, vitamin $B_{12}$ and ascorbic acid, and fat-soluble vitamins such as vitamin A, vitamin D, vitamin E, and vitamin K. Exemplary lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

The analyte or enzyme to be detected may be a marker for a biological pathway, a stage of cell cycle, a cell type, a tissue type, an organ type, a developmental stage, a disease, disorder or infection type or stage, or drug or other treatments. Exemplary tissues include connective, epithelium, muscle or nerve tissues. Exemplary organs include an accessory organ of the eye, annulospiral organ, auditory organ, Chievitz organ, circumventricular organ, Corti organ, critical organ, enamel organ, end organ, external female gential organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmuller, sense organ, organ of smell, spiral organ, subcommissural organ, subfornical organ, supernumerary organ, tactile organ, target organ, organ of taste, organ of touch, urinary organ, vascular organ of lamina terminals, vestibular organ, vestibulocochlear organ, vestigial organ, organ of vision, visual organ, vomeronasal organ, wandering organ, Weber organ and organ of Zuckerkandl. Exemplary internal animal organs include brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels. Exemplary diseases or disorders include neoplasm (neoplasia), cancers, immune system diseases or disorders, metabolism diseases or disorders, muscle and bone diseases or disorders, nervous system diseases or disorders, signal diseases or disorders, transporter diseases or disorders.

Methods of Use

The devices of the invention are useful for determining the concentration of an analyte in a fluid sample. When the fluid sample is blood, and the analyte of interest is glucose, a small blood sample is drawn from the patient, who in this embodiment will usually obtain the sample by pricking their finger to obtain a blood droplet. The device can be touched to the droplet at the sample intake port 201 after the device is inserted into the reading port of an electronic reader (e.g., a VMP potentiostat) and voltage applied. The electrical contacts on the meter contact the corresponding contact leads on the device. The sample is drawn into the reaction area either by wicking through the hydrophilic porous material, and/or by capillary action pulling sample fluid into the reaction chamber. The reader then provides a reading and the result is determined by the operator.

Method of Manufacture

A material is obtained from which the base plate is formed. Electrodes are disposed on the base plate. The electrodes can be formed using materials as described above, and can be disposed on the base plate by screen printing or any suitable method. The electrodes can be applied as a paste or in another suitable form. An insulating layer is applied to the base plate in some embodiments, although not every embodiment utilizes an insulating layer. When the insulating layer is a dielectric ink, it also can be applied by screen printing or any of the methods described herein. The insulating layer can have a groove and be applied to the base plate, so that the electrodes are present in the groove, which is surrounded by the insulating layer.

A hydrophilic porous material is then applied to the base layer or insulating layer. The hydrophilic porous material can cover all or only a portion of the base plate or insulating material. If the hydrophilic porous material covers only a portion of the base plate, it should cover the area where the reagent is deposited in the reaction area, and the groove in the insulating layer (if present). It can also cover the opening in the cover, when the cover is placed. When the insulating layer and cover both have a groove, the grooves can be aligned. A hydrophobic protective layer is then affixed to the hydrophilic porous material. This again can be affixed by adhesive present on either the porous hydrophilic material or the protective layer, or both. A cover is also affixed to the device. The cover is affixed so that the opening in the cover is in alignment with the groove on the insulating layer (if present), thereby providing for communication between the electrodes and the exterior of the device. When the cover is a dielectric ink, it can be screen printed on the hydrophobic protective layer, or affixed by any of the methods described herein. The device can also be configured so that the hydrophilic porous material and the hydrophobic protective layer do not have their own adhesive layer(s), but that the cover is a dielectric ink, which is applied to the hydrophobic protective layer and hydrophilic porous material underneath (and insulating layer if present). The cover can be applied so that it penetrates the pores of the hydrophobic protective layer and hydrophilic porous material, and thereby affixes these members to the device.

EXAMPLE 1

Construction of a Sensor

This example illustrates the construction of a sensor of the invention. A 14 mil chip of print-treated PET was selected to form the base plate. Ag/AgCl ink was printed onto the PET base to form the contact leads, conductive leads, and reference electrode of the electrode system, followed by heating to dry. Conductive carbon ink was then printed to form the conductive leads, contacts, counter and working electrodes of the electrode system, followed by heating to dry (FIG. 1). A PET insulating layer sandwiched with acrylic pressure sensitive adhesive (PSA) and silicone release layers on both sides was laser cut to form the insulating layer 111. By peeling away one side of the release layer, the pressure sensitive adhesive (PSA) PET insulating layer was superimposed onto the base plate having the conductive electrodes. Optionally, the PSA PET can be replaced with a screen printed carbon insulating layer having the groove 113. Peeling away another release layer of the PSA PET insulating layer exposes the groove. A reagent fluid mixture was jet dispensed inside the groove and then dried at 65° C. for 5 minutes to form the reagent layer (not shown in FIG. 1).

A hydrophilic porous mesh 115 and a hydrophobic protective mesh 117 was then deposited to cover the microfluidic channel. Optionally an integrated hydrophilic/hydrophobic mesh can be used in place of the hydrophilic porous material and protective layer. Another layer of PSA PET was followed to construct the cover of the biosensor (FIG. 1). A carbon black screen printed layer can also be used instead of the PSA PET to form the cover.

EXAMPLE 2

This example illustrates a use of the invention in the detection of blood glucose levels. A device was manufactured as described in Example 1 containing a dried reagent present in the reaction chamber and having the following components: a phosphate buffer solution in which is dissolved at least one hydrophilic polymer such as cellulose, a low disaccharide trehalose stabilizer, a Triton X-100 surfactant, a ferricyanide mediator and glucose oxidase enzyme. This reagent was selected to test for the presence and quantity of glucose in whole blood.

A three electrode system was used in this embodiment and the reagent film covered all three electrodes. It is estimated that when sample is applied to the sensor, it will be brought into contact with all three electrodes within 1 second. The hydrophobic protective layer served to prevent contamination of the sample with sweat or oils from the operator's hands.

The sensor was inserted into the insertion port of a VMP Potentiostat. A voltage of +0.4 V was applied to the working electrode relative to the reference electrode, and then a sample of whole blood was applied. Twenty seconds after the blood sample was applied to the working electrode, current flowing across the working and the counter electrodes was measured.

Figure 5:
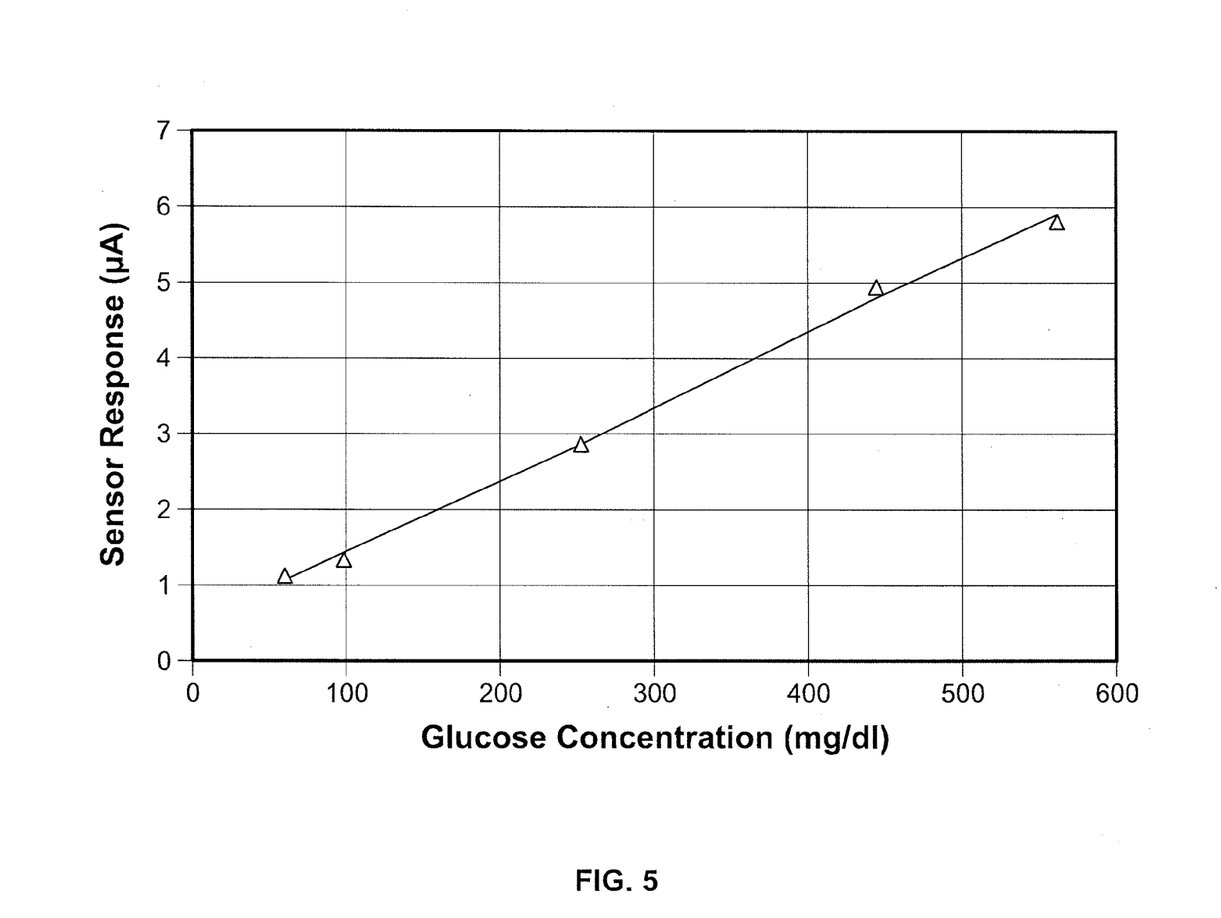
FIG. 5 provides a graphical illustration of the results of assays using a device of the invention.

Current values were obtained from various samples containing various concentrations of glucose. FIG. 5 provides a graphical illustration of the response characteristics of the glucose sensor to the different sample solutions. As indicated in FIG. 5, a linear and statistical correlation was obtained.

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The invention claimed is:

1. A microfluidic device for determining an amount of an analyte in a sample, comprising:
   a base plate comprising a proximal and a distal end and having at least three electrodes printed thereon, wherein the at least three electrodes comprise a counter electrode, positioned at the proximal end of the base plate, a reference electrode, positioned furthest from the proximal end of the base plate, and a working electrode, positioned in between the counter and reference electrodes;
   a reaction layer on at least one of the electrodes comprising reagents for producing a detectable signal in response to a quantity of analyte in the sample;
   an insulating layer positioned between the base plate and a hydrophilic layer, wherein the insulating layer comprises a groove,
   a hydrophilic layer comprising a porous material and configured for holding a liquid sample in contact with the base plate;
   a hydrophobic mesh protective layer disposed directly on the hydrophilic porous material, wherein the hydrophobic protective layer is configured for retaining the sample in contact with the reaction layer and at least covers said proximal end where said at least three electrodes are positioned;
   a cover made of a dielectric material and having a proximal end and a distal end comprised on the hydrophobic protective layer and containing a groove providing for communication between the electrodes and the exterior of the device, which groove aligns with the corresponding groove in the insulating layer.

2. The device of claim 1, wherein the insulating layer comprises a hydrophobic, dielectric material.

3. The device of claim 2 wherein the cover and insulating layer are comprised of a non-conductive material selected from the group consisting of an ink, adhesive, adhesive tape, a plastic, a celluloid material, glass, and a non-conductive foil; and
   wherein the opening in the cover comprises a second groove extending from the proximal to the distal end of the device and is aligned with the groove of the insulating layer.

4. The device of claim 2 wherein the base plate, groove, and hydrophilic porous material define a reaction chamber, and the reaction layer is comprised within the reaction chamber.

5. The device of claim 1 wherein the base plate is made of a material selected from the group consisting of carbon, polystyrene, polycarbonate, and a polyester.

6. The device of claim 1 wherein the hydrophilic porous material is selected from the group consisting of: a gel, glass fiber, a porous plastic, polyester, a mesh, a cellulose material, and a polyester.

7. The device of claim 6 wherein the hydrophilic porous material is a mesh.

8. The device of claim 1 wherein the protective layer is comprised of a material selected from the group consisting of: a glass fiber, porous plastics, cellulose material, and a polyester.

9. The device of claim 1 wherein the cover is comprised of a hydrophobic, non-conductive material selected from the group consisting of: an ink, adhesive, adhesive tape, a plastic, a celluloid material, glass, and a non-conductive foil.

10. The device of claim 1 wherein the protective layer is situated between the hydrophilic porous material and the cover, and extends across the opening in the cover.

11. The device of claim 1 wherein the reaction layer comprises glucose oxidase.

12. The device of claim 1 wherein the hydrophilic porous material is disposed on the base plate, the hydrophobic protective layer is disposed on the hydrophilic porous material, and the cover is disposed on at least the hydrophobic protective layer.

13. A method of manufacturing a microfluidic device, comprising:
- providing a base plate and screen printing an electrode system thereon, wherein the electrode system comprises three electrodes, and further wherein the at least three electrodes comprise a counter electrode, positioned at the proximal end of the base plate, a reference electrode, positioned furthest from the proximal end of the base plate, and a working electrode, positioned in between the counter and reference electrodes;
- placing a reagent formulation for conducting an assay onto at least one electrode of the electrode system;
- applying an insulating layer to the base plate, wherein the insulating layer comprises a groove;
- applying a hydrophilic porous material to the insulating layer;
- affixing a non-porous hydrophobic mesh protective layer directly to the hydrophilic porous material, wherein the hydrophobic protective layer at least covers a portion of said base plate comprising said electrode system;
- affixing a cover made of a dielectric material and having a proximal end and a distal end to the hydrophobic protective layer, wherein the cover contains a groove providing communication between the electrodes and the exterior of the device, and
- aligning the groove of the cover with the groove of the insulating layer.

14. The method of claim 13, wherein the insulating layer is comprised of a hydrophobic, dielectric material.

15. The method of claim 13 wherein the insulating layer is placed by a method selected from the group consisting of screen printing, ink jet printing, application of adhesive or adhesive tape, lamination of the layers of material, heat sealing, and ultrasonic welding.

16. The method of claim 13 wherein the base plate is made of a material selected from the group consisting of: carbon, polystyrene, polycarbonate, and a polyester.

17. The method of claim 13 wherein the hydrophilic porous material is selected from the group consisting of: a gel, glass fiber, a porous plastic, cellulose, a mesh, a gel, a glass fiber, a porous plastic, a cellulose material, and a polyester.

18. The method of claim 13 wherein the hydrophobic protective layer is comprised of a material selected from the group consisting of: a glass fiber, porous plastics, cellulose material, and polyester, and
- the hydrophobic protective layer is situated between the hydrophilic porous material and the cover; and
- the opening in the proximal end of the cover is a groove, and the hydrophobic protective layer extends across the groove.

19. The method of claim 13 wherein the cover is comprised of a hydrophobic non-conductive material selected from the group consisting of an ink, adhesive, adhesive tape, a plastic, a celluloid material, glass, and a non-conductive foil.

20. The method of claim 13 wherein the hydrophilic porous material and the hydrophobic protective layer are placed to cover at least the proximal portion of the base plate, and the at least two electrodes communicate with the exterior of the device through the opening in the proximal end of the cover.

21. The method of claim 13 wherein the hydrophilic porous material is placed on the base plate by a method selected from the group consisting of: screen printing, ink jet printing, application of adhesive or adhesive tape, lamination of the layers of material, heat sealing, and ultrasonic welding.

22. The method of claim 13 wherein the hydrophobic protective layer and/or cover are placed by a method selected from the group consisting of: screen printing, ink jet printing, application of adhesive or adhesive tape, lamination of the layers of material, heat sealing, and ultrasonic welding.

23. A method of determining the concentration of an analyte in a fluid sample comprising:
- placing a portion of the sample on a test device comprising:
  - a base plate having a proximal and a distal end and comprising an electrode system screen printed thereon, wherein the electrode system has at least three electrodes comprising a counter electrode, positioned at the proximal end of the base plate, a reference electrode, positioned furthest from the proximal end of the base plate, and a working electrode, positioned in between the counter and reference electrodes;
  - a reaction layer on at least one of the electrodes comprising materials for producing a detectable signal in response to a quantity of analyte in the sample;
  - an insulating layer positioned between the base plate and a hydrophilic layer, wherein the insulating layer comprises a groove,
  - a hydrophilic layer comprising a porous material and configured for wicking a liquid sample into contact with the first layer;
  - a non-porous hydrophobic mesh protective layer disposed directly on the wicking material, wherein the hydrophobic protective layer is configured for retaining the sample in contact with the reaction layer and at least covers a portion of said base plate comprising said at least three electrodes; and
- a cover made of a hydrophobic, dielectric material and having a proximal and a distal end comprised on the hydrophobic protective layer and containing a groove providing for communication between the electrodes and the exterior of the device, wherein the groove aligns with the corresponding groove in the insulating layer;
- inserting the test device into an electronic detection system so that the test device is connected to the detection system through the contact leads of the test device;
- determining the concentration of the analyte in the fluid sample.

24. The method of claim 23 wherein:
- the insulating layer is comprised of a hydrophobic, dielectric material.

25. The method of claim 23 wherein
- the base plate is made of a material selected from the group consisting of: carbon, polystyrene, polycarbonate, and a polyester;
- the hydrophilic porous material is a material selected from the group consisting of: a gel, glass fiber, a porous plastic, a cellulosic material, and a polyester;
- the hydrophobic protective layer is comprised of a material selected from the group consisting of: a glass fiber, a porous plastic, a cellulosic material, and a polyester; and
- the cover and insulating layer are comprised of a non-conductive material selected from the group consisting of an ink, adhesive, adhesive tape, a plastic, a celluloid material, glass, and a non-conductive foil.

* * * * *